(12) United States Patent
Yamamoto et al.

(10) Patent No.: US 10,575,769 B2
(45) Date of Patent: Mar. 3, 2020

(54) DATA-ORIENTED FEEDBACK CONTROLLER AND DATA-ORIENTED FEEDBACK CONTROL METHOD

(71) Applicant: HIROSHIMA UNIVERSITY, Hiroshima (JP)

(72) Inventors: Toru Yamamoto, Hiroshima (JP); Takuya Kinoshita, Hiroshima (JP)

(73) Assignee: HIROSHIMA UNIVERSITY, Hiroshima (JP)

( * ) Notice: Subject to any disclaimer, the term of this patent is extended or adjusted under 35 U.S.C. 154(b) by 39 days.

(21) Appl. No.: 15/690,261

(22) Filed: Aug. 29, 2017

(65) Prior Publication Data
US 2018/0055403 A1    Mar. 1, 2018

(30) Foreign Application Priority Data
Aug. 30, 2016    (JP) .................................. 2016-168079

(51) Int. Cl.
| | | |
|---|---|---|
| *G06F 19/00* | (2018.01) | |
| *A61B 5/16* | (2006.01) | |
| *G05B 11/42* | (2006.01) | |
| *G05B 13/04* | (2006.01) | |
| *A61B 5/053* | (2006.01) | |

(Continued)

(52) U.S. Cl.
CPC .............. *A61B 5/165* (2013.01); *A61B 5/16* (2013.01); *G05B 11/42* (2013.01); *G05B 13/041* (2013.01);
(Continued)

(58) Field of Classification Search
CPC ......... A61B 5/165; A61B 5/16; A61B 5/4851; A61B 5/0816; A61B 5/0533;
(Continued)

(56) References Cited

U.S. PATENT DOCUMENTS 7,942,816 B2 *  5/2011  Satoh .................... A61B 5/165
                                                             600/300
8,473,044 B2 *  6/2013  Lee ...................... A61B 5/0476
                                                             600/544
(Continued)

FOREIGN PATENT DOCUMENTS

JP        H11-65422 A     3/1999
JP        4825960 B2      11/2011

*Primary Examiner* — Michael D Masinick
(74) *Attorney, Agent, or Firm* — Maschoff Brennan

(57) ABSTRACT

A data-oriented feedback controller disclosed herein allows the user to wear or use a device under control comfortably, and includes: a device under control for determining a controlled variable $\theta(t)$ with respect to a human being in accordance with an input manipulated variable $u(t)$; a primary controller for determining the manipulated variable $u(t)$ based on an input difference $v(t)$ between an estimated target value $w(t)$ and the controlled variable $\theta(t)$; a psychological evaluator for detecting biometric information $bio(t)$ about the human being corresponding to the controlled variable $\theta(t)$, evaluating the human being's psychology based on the biometric information $bio(t)$, and determining a psychological output value $y(t)$ representing the psychology; and a secondary controller for receiving a difference $\varepsilon(t)$ between a target value $r(t)$ of the human being's psychology and the psychological output value $y(t)$ and determining the estimated target value $w(t)$ based on the difference $\varepsilon(t)$.

3 Claims, 8 Drawing Sheets

(51) Int. Cl.
    *A61B 5/0476*      (2006.01)
    *A61B 5/08*      (2006.01)
    *A61B 5/04*      (2006.01)
    *A61B 5/024*      (2006.01)
    *A61B 5/00*      (2006.01)
    *A61B 5/0488*      (2006.01)

(52) U.S. Cl.
    CPC ........... *A61B 5/024* (2013.01); *A61B 5/04012* (2013.01); *A61B 5/0476* (2013.01); *A61B 5/0488* (2013.01); *A61B 5/0533* (2013.01); *A61B 5/0816* (2013.01); *A61B 5/4851* (2013.01); *G05B 2219/40305* (2013.01)

(58) Field of Classification Search
    CPC ... A61B 5/0476; A61B 5/04012; A61B 5/024; A61B 5/0488
    See application file for complete search history.

(56) References Cited

U.S. PATENT DOCUMENTS

| | | | |
|---|---|---|---|
| 8,973,022 B2* | 3/2015 | Lee | G09B 7/02 |
| | | | 382/118 |
| 9,292,858 B2* | 3/2016 | Marci | G06Q 30/0201 |
| 9,351,658 B2* | 5/2016 | Lee | A61B 5/0006 |
| 2007/0050151 A1* | 3/2007 | Satoh | A61B 5/165 |
| | | | 702/19 |
| 2007/0167690 A1* | 7/2007 | Miyazaki | A61B 5/16 |
| | | | 600/300 |
| 2016/0155443 A1* | 6/2016 | Khan | G06F 1/3203 |
| | | | 704/275 |
| 2018/0055403 A1* | 3/2018 | Yamamoto | A61B 5/04888 |

* cited by examiner

DATA-ORIENTED FEEDBACK CONTROLLER AND DATA-ORIENTED FEEDBACK CONTROL METHOD

CROSS-REFERENCE TO RELATED APPLICATION

This application claims priority to Japanese Patent Application No. 2016-168079 filed on Aug. 30, 2016, the entire disclosure of which is hereby incorporated by reference.

BACKGROUND

The present disclosure relates to a data-oriented feedback controller and a data-oriented feedback control method.

Japanese Patent No. 4825960 discloses a controller for controlling the temperature, pressure, or any other physical condition of the object of control by adjusting control parameters based on data accumulated.

Japanese Unexamined Patent Publication No. 11-65422 discloses a psychological evaluation method for properly controlling the details of the work by collecting biometric information from an eye blink sensor or a galvanic skin resistance sensor.

However, the controller disclosed in Japanese Patent No. 4825960 is not intended to be applied to a human being and does not use data about human psychology, either. Meanwhile, the controller disclosed in Japanese Unexamined Patent Publication No. 11-65422 collects biometric information from an eye blink sensor or a galvanic skin resistance sensor, but does not indicate how to use the information as feedback parameters and how to guide the human to the best psychological status.

As can be seen, there have been no controllers operating while taking human psychology (such as the degree of comfort and sensitivity) into account. An ankle foot orthosis, an assist device, and other wearable robotic devices do perform feedback control. However, those devices do not use the psychology of the human wearer (including the degree of comfort or sensitivity) as data. Thus, no wearable robotic devices have ever been provided which are comfortable enough to wear or use for users.

The present disclosure provides a data-oriented feedback controller, e.g., a controller for controlling an ankle foot orthosis or any other device under control to be worn or used by a human user (i.e., a non-linear object), which allows him or her to wear or use the device more comfortably by performing not only control over a physical quantity but also feedback control on the human psychology (such as sensitivity) as well. The present disclosure also provides a data-oriented feedback control method using such a controller.

SUMMARY

A data-oriented feedback controller according to an aspect of the present disclosure includes: a device under control configured to determine a controlled variable $\theta(t)$ with respect to a human being in accordance with an input manipulated variable $u(t)$; a primary controller configured to determine the manipulated variable $u(t)$ based on an input difference $v(t)$ between an estimated target value $w(t)$ and the controlled variable $\theta(t)$; a psychological evaluator configured to detect biometric information $bio(t)$ about the human being corresponding to the controlled variable $\theta(t)$, evaluate the human being's psychology based on the biometric information $bio(t)$, and determine a psychological output value $y(t)$ representing the psychology; and a secondary controller configured to receive a difference $\varepsilon(t)$ between a target value $r(t)$ of the human being's psychology and the psychological output value $y(t)$ and determine the estimated target value $w(t)$ based on the difference $\varepsilon(t)$.

A data-oriented feedback control method according to another aspect of the present disclosure includes: determining, by a device under control, a controlled variable $\theta(t)$ with respect to a human being in accordance with an input manipulated variable $u(t)$; determining, by a primary controller, the manipulated variable $u(t)$ based on an input difference $v(t)$ between an estimated target value $w(t)$ and the controlled variable $\theta(t)$; detecting, by a psychological evaluator, biometric information $bio(t)$ about the human being corresponding to the controlled variable $\theta(t)$, evaluating the human being's psychology based on the biometric information $bio(t)$, and determining a psychological output value $y(t)$ representing the psychology; and determining, by a secondary controller, the estimated target value $w(t)$ based on a difference $\varepsilon(t)$ between a target value $r(t)$ of the human being's psychology and the psychological output value $y(t)$.

According to the present disclosure, biometric information about a human being, such as the degree of comfort or sensitivity, is detected from a device under control such as an ankle foot orthosis to evaluate the human being's psychology, and a value representing the psychology is used as a control parameter, thus providing a data-oriented feedback controller and data-oriented feedback control method allowing the user to wear or use the device sufficiently comfortably.

DETAILED DESCRIPTION

Embodiments of the present disclosure will now be described in detail with reference to the drawings as needed. Note that excessively detailed description will sometimes be omitted herein to avoid complexity. For example, detailed description of a matter already well known in the art and redundant description of substantially the same configuration will sometimes be omitted herein. This will be done to avoid redundancies in the following description and facilitate the understanding of those skilled in the art.

Note that the present inventors provide the following detailed description and the accompanying drawings only to help those skilled in the art fully appreciate the present disclosure and do not intend to limit the scope of the subject matter of the appended claims by that description or those drawings.

First and second embodiments of the present disclosure will be described in this order in terms of their circuit configuration, data control, and other details.

(1) First Example

This embodiment includes essential components according to the present disclosure.

(Overall Circuit Configuration)

Figure 1:
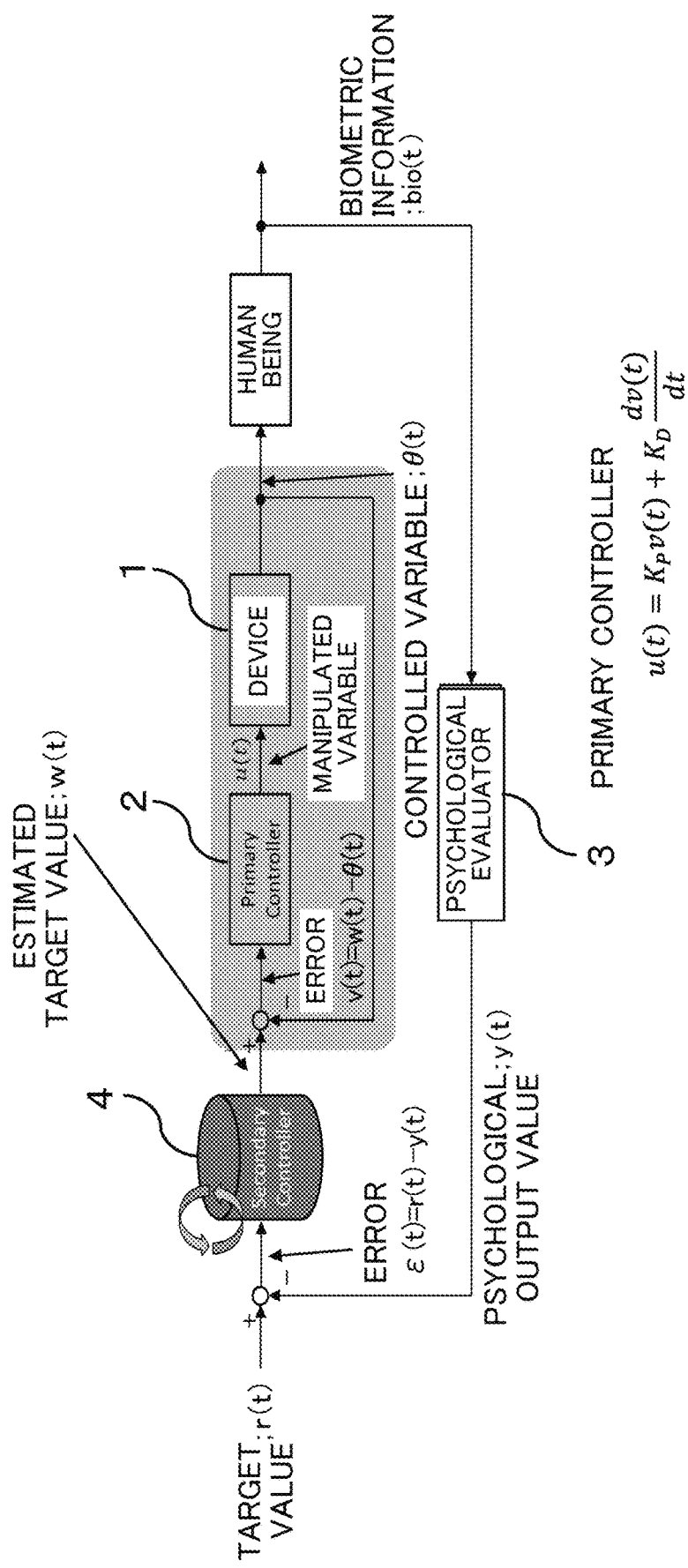
FIG. 1 illustrates an overall configuration for a first embodiment of the present disclosure.

FIG. 1 illustrates essential components according to the present disclosure. In FIG. 1, a device under control 1 determines a controlled variable θ(t) with respect to a human being in accordance with an input manipulated variable u(t). A primary controller 2 determines the manipulated variable u(t) with respect to the device under control 1 based on an input difference v(t) between an estimated target value w(t) and the controlled variable θ(t). A psychological evaluator 3 detects biometric information bio(t) about the human being corresponding to the controlled variable θ(t), evaluates the human being's psychology based on the biometric information bio(t), and determines a psychological output value y(t) representing the psychology. A secondary controller 4 determines the estimated target value w(t) based on an input difference ε(t) between a target value r(t) of the human being's psychology and the psychological output value y(t).

In this case, the input and output values of the primary controller 2 are subjected to PD control to meet the following Equation (1). In this PD control, fixed constants are used as the gains $K_{P1}$ and $K_{D1}$.

$$u(t) = K_{P1}v(t) + K_{D1}\frac{dv(t)}{dt} \quad (1)$$

In general, when PID control is performed, integral action is also taken into consideration. In this example, however, PD control is supposed to be performed for convenience sake with no integral action taken into account. This is because a device to be worn by a human being, such as the ankle foot orthosis to be described later, is controllable easily enough by the PD control with no integral action taken into account. If the device under control 1 is an air conditioner, for example, control of the temperature in a room by controlling the air conditioner according to the human psychology requires taking an integral action into account. Therefore, a determination may be made appropriately depending on the necessity of an integral action whether the device under control 1 should be subjected to PID control or PD control. In this example, the gains $K_{P1}$ and $K_{D1}$ are supposed to be fixed constants for convenience sake when the PD control is performed. However, these gains may be variable depending on the type of the device under control 1.

On the other hand, the input and output values of the secondary controller 4 are subjected to PID control to meet the following Equation (2). The details of this control will be described later.

$$w(t) = -K_P y(t) + K_I \int_0^\tau \varepsilon(\tau)d\tau - K_D \frac{dy(t)}{dt} \quad (2)$$

As can be seen, this embodiment uses, as a control parameter, a psychological output value y(t) obtained based on the biometric information bio(t) about a human being, thus providing a controller operating while taking the human being's psychology (such as the degree of comfort or sensitivity) into account.

(Biometric Information Detection 1)

Examples of means for detecting the biometric information bio(t) about a human being include facial expression detection by a CCD camera, heart rate detection by a heart rate sensor, respiration (e.g., respiration rate and depth) detection by a CCD camera, galvanic skin resistance detection by a skin impedance sensor, upper- and lower-limb muscle potential detection by a myoelectric sensor, and audio information detection by a microphone. The biometric information may be detected at any appropriate timing with one, two or more detection means.

(Biometric Information Detection 2)

Next, "sensitivity" will be described as an exemplary piece of biometric information bio(t) about a human being.

A human being may have a feeling or emotion such as a sense of excitement, exhilaration, suspense, or a flutter on seeing or hearing something or on touching something or being touched by someone. The present inventors believe that these feelings or emotions are brought about by complex, higher cerebral activities of a human being, and that a somatic nervous system including motor nerves and sensory nerves, an autonomic nervous system including sympathetic nerves and parasympathetic nerves, memories, experiences, and other factors are major contributing factors in the formation of these feelings or emotions. The present inventors define sensitivities as a higher cerebral function of synthesizing together exteroceptive information (somatic nervous system) and interoceptive information (autonomic nervous system) and looking down upon an emotional reaction produced by reference to past experiences and memories from an even higher level. In other words, the "sensitivity" can be said to be a higher cerebral function allowing a person to intuitively sense the gap between his or her prediction (image) and the result (sense information) by comparing it to his or her past experiences and knowledge.

Viewing the sensitivity that is such a higher cerebral function in perspective requires grasping the sensitivity comprehensively from various points of view or aspects.

For example, the sensitivity may be grasped from a "pleasant/unpleasant" point of view or aspect by determining whether the person is feeling fine, pleased, or comfortable, or otherwise, feeling sick, displeased, or uncomfortable.

Alternatively, the sensitivity may also be grasped from an "active/inactive" point of view or aspect by determining whether the person is awaken, heated, or active, or otherwise, absent-minded, calm, or inactive.

Still alternatively, the sensitivity may also be grasped from a "sense of expectation" point of view or aspect by determining whether the person is excited with the expectation or anticipation of something, or otherwise, unexcited.

A Russell's circular ring model, plotting the "pleasant/unpleasant" and "active/inactive" parameters on dual axes, is known. The feelings can be represented by this circular ring model. The present inventors believe that the sensitivity is a higher cerebral function of comparing the gap between the prediction (image) and the result (sense information) to experiences and knowledge, and therefore, cannot be sufficiently represented by the traditional circular ring model comprised of the two axes indicating pleasant/unpleasant and active/inactive, respectively. Thus, the present inventors grasp the sensitivity as a multi-axis sensitivity model in which the time axis (indicating a sense of expectation, for example) is added as a third axis to the Russell's circular ring model.

Figure 2:
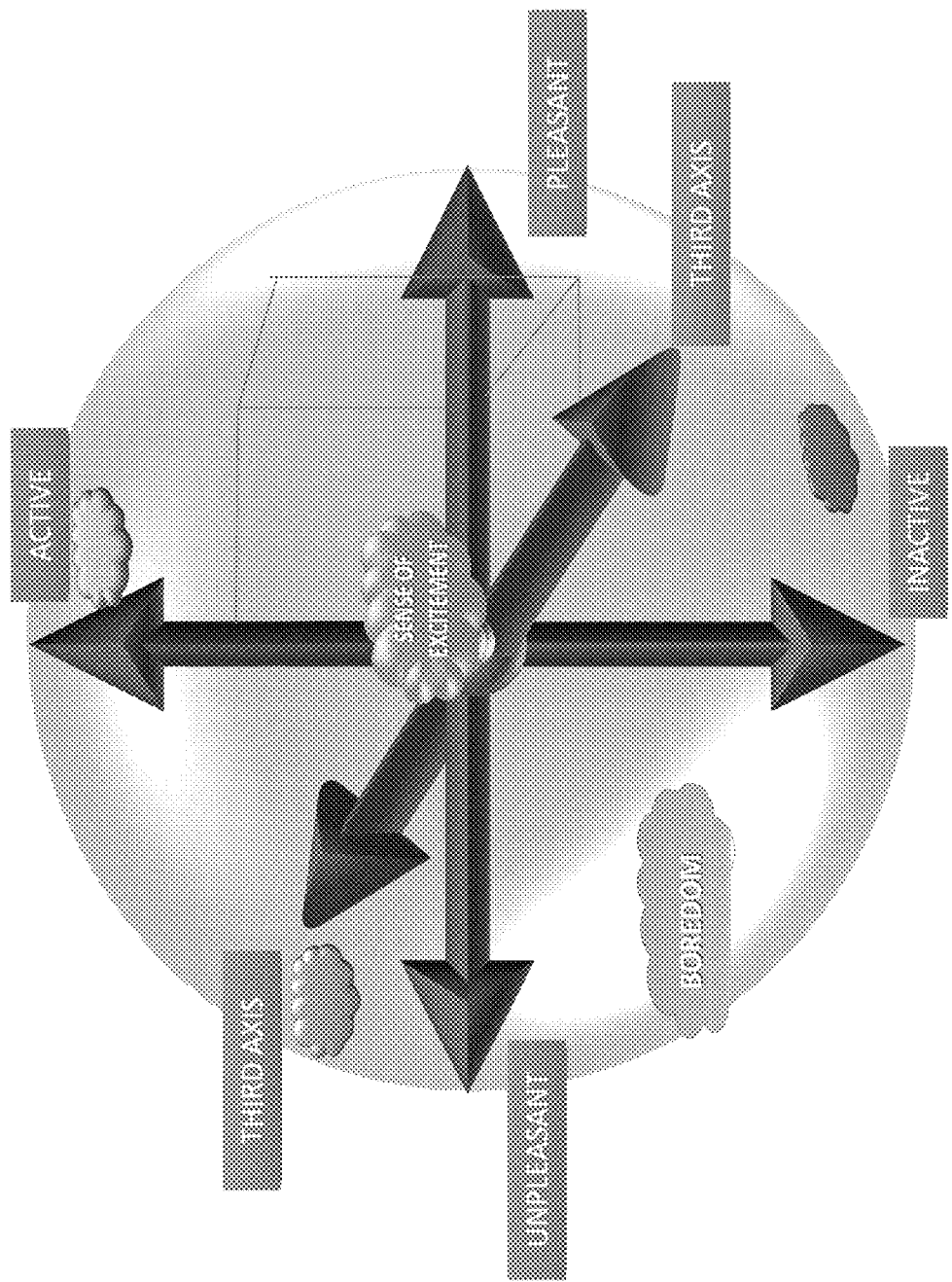
FIG. 2 illustrates a multi-axis sensitivity model diagram.

FIG. 2 is a schematic representation illustrating a multi-axis sensitivity model adopted in the present disclosure. The multi-axis sensitivity model may be represented with "pleasant/unpleasant" plotted as a first axis, "active/inactive" plotted as a second axis, and "time (sense of expectation)" plotted as a third axis. An advantage of representing the sensitivity as such a multi-axis model is enabling a quantitative evaluation (i.e., visualization) of sensitivity, which is a vague and broad concept, by calculating evaluation values on respective axes and by synthesizing those evaluation values together. Specifically, it has been proved that the sensitivity value can be evaluated by the following equation by obtaining cerebral physiological indices (namely, $EEG_{pleasant}$, $EEG_{active}$, $EEG_{expectation}$) for respective axes based on the cerebral physiological information of respective axes of the multi-axis sensitivity model and by using subjective psychological axes indicating the weighting coefficients (a, b, c) of respective axes of the multi-axis sensitivity model that have been obtained based on subjective statistical data of the subjects.

sensitivity value=[subjective psychological axes]*
[cerebral physiological indices]=$a*EEG_{pleasant}$+
$b*EEG_{active}$+$c*EEG_{expectation}$ Thus, using this sensitivity value as the psychological output value y(t) will provide a data-oriented feedback controller that takes human sensitivity into account.

(Data Control)

1. Procedure of Design of Secondary Controller 4

In this embodiment, the secondary controller 4 is designed in the following procedure.

[STEP 1] Compiling Initial Database

According to data-oriented control, no PID gains can be calculated in principle if there are no accumulated data of the past. Therefore, an initial database is compiled with appropriate PID gains used and with an information vector generated based on input and output data and the PID gains.

$$\phi_I(j)=[\overline{\phi}(j),K(j)]$$

$$(j=1,2,\ldots,N,\ i=1,2,\ldots,M) \quad (3)$$

This Equation (3) represents the data in the secondary controller 4 at a time j.

Furthermore, $\overline{\phi}(j)$ and $K(j)$ are given by the following Equations (4):

$$\overline{\phi}(t):=[r(t+1),r(t)y(t),\ldots,y(t-n_y+1),w(t-1),\\ w(t-1),\ldots,w(t-n_u+1)]$$

$$K(t)=[K_P(t),K_I(t),K_D(t)] \quad (4)$$

In these equations, N indicates the number of data items (i.e., the number of information vectors in the initial database). Since the PID gains are fixed in the initial database, $K(1)=K(2)=\ldots=K(N)$ is satisfied.

As can be seen from these equations, at a time t, target values r(t+1), psychological output values y(t), past psychological output values y(t−1), . . . , past estimated target values w(t−1), . . . and latest PID gains K(t) are accumulated in the database in the secondary controller 4.

[STEP 2] Selecting Distance and Neighborhood

The distance from a point of request $\overline{\phi}(t)$ to the information vector $\overline{\phi}(j)$ accumulated in the database is obtained by a weighted $L_1$ norm represented by the following Equation (5):

$$d(\overline{\phi}(t),\overline{\phi}(j)) = \sum_{i=1}^{n_y+n_u+1} \left| \frac{\overline{\phi}_l(t) - \overline{\phi}_l(j)}{\max\overline{\phi}_l(m) - \min\overline{\phi}_l(m)} \right| \quad (5)$$

$$(j=1,2,\ldots,N)$$

In this Equation (5), $\overline{\phi}_l(j)$ indicates the $l^{th}$ element of the $j^{th}$ information vector. Likewise, $\overline{\phi}_l(t)$ indicates the $l^{th}$ element of the point of request at a time t. Furthermore, max $\overline{\phi}_l(m)$ indicates the greatest one of the respective $l^{th}$ elements of all information vectors ($\overline{\phi}(j)$, j=1, 2, . . . , N) in the database, and min $\overline{\phi}_l(m)$ indicates its minimum value. Now k information vectors are selected from the vectors with shortest distances d obtained by the above equation, and a set of those selected data is defined as neighborhood. Based on this distance data, the PID gains at a certain point in time are replaced with newest data.

[STEP 3] Forming Local Controller

Next, with respect to the neighborhood selected in STEP 2, a local controller is formed by the linearly weighted average (LWA) method represented by the following Equation (6):

$$K(t)=\Sigma_{i=1}^{k}\omega_i K(i),\Sigma_{i=1}^{k}\omega_i=1 \quad (6)$$

In this Equation (6), $\omega_i$ indicates the weight added to K(i) included in the $i^{th}$ information vector selected, and is given by the following Equation (7):

$$\omega_i = \frac{\frac{1}{d(\overline{\phi}(t),\overline{\phi}(j))}}{\sum_{j=1}^{k}\left(\frac{1}{d(\overline{\phi}(t),\overline{\phi}(j))}\right)} \quad (7)$$

Under this procedure, the PID gains at each point in time can be calculated. Note that to appropriately adjust the PID gains with such a data-oriented PID control system, database learning (i.e., update of control parameters) needs to be performed. Thus, according to this embodiment, the fictitious reference iterative tuning (FRIT) method is adopted in which PID gains in each data set in the database are updated offline in advance through learning based on the initial data used to establish the database. Therefore, applying this [STEP 3] after the offline update allows the updated PID gains to be applied to the control system.

Such a method of updating data offline significantly cuts down the computational time compared to updating data online, which is one of its advantages to be achieved by this embodiment.

2. Offline Processing by FRIT Method

Figure 3:
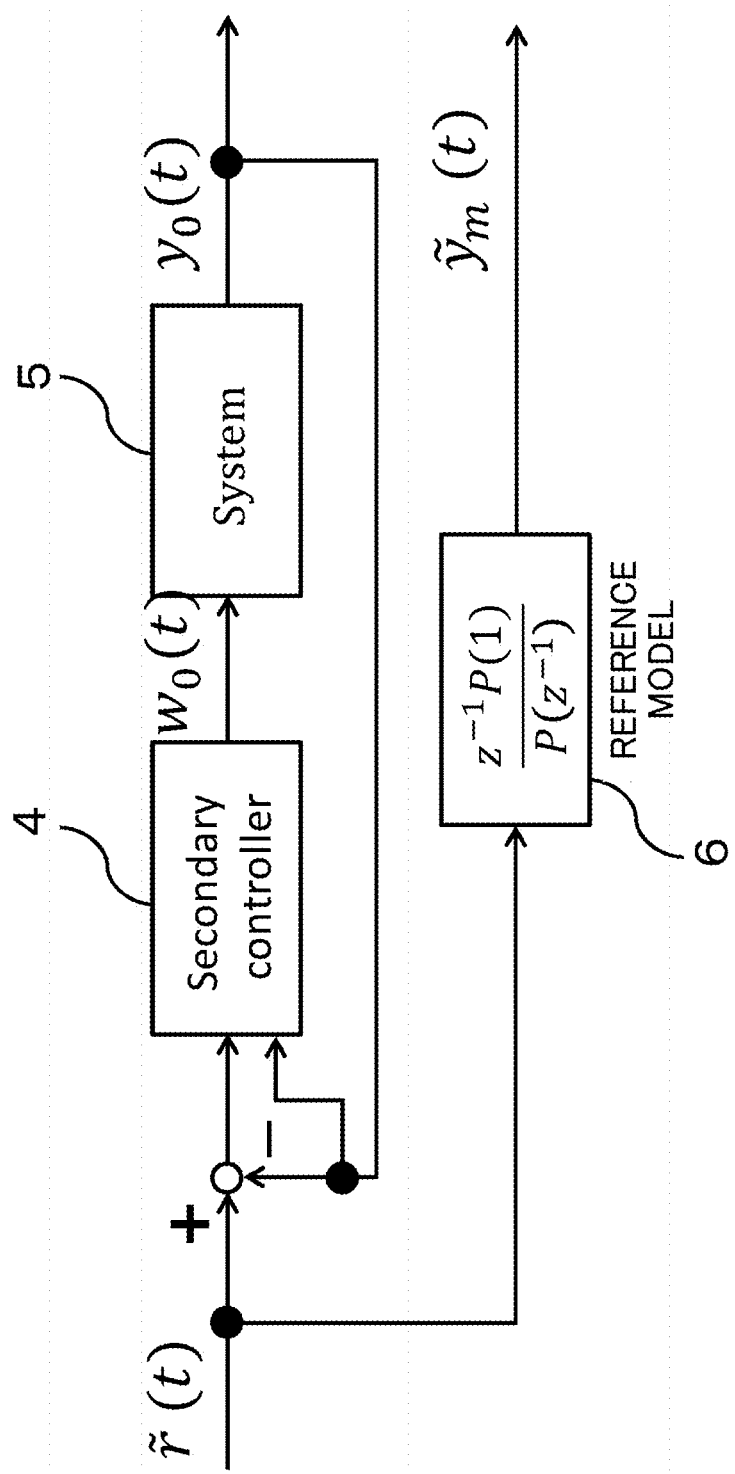
FIG. 3 illustrates a configuration for a circuit for calculating a control parameter by analysis according to the FRIT method.

FIG. 3 illustrates a method for directly calculating control parameters for a controller based on the input/output data $w_0(t)$, $y_0(t)$ obtained by a single experiment and a pseudo reference input $\tilde{r}(t)$ generated from these data. In FIG. 3, the reference sign 4 denotes a secondary controller, the reference sign 5 denotes a system comprised of a device under control and a primary controller, and the reference sign 6 denotes a reference model generator. This output $\tilde{y}_m(t)$ is used to generate the latest control parameters.

In this case, the input and output values of the secondary controller 4 satisfy the following Equation (8):

$$\Delta w_0(t)=K_I(t)\{\tilde{r}(t)-y_0(t)\}-K_P\Delta y_0(t)-K_D(t)\Delta^2 y_0(t) \quad (8)$$

Therefore, the target value $\tilde{r}(t)$ may be calculated based on the experimental data by the following Equation (9):

$$\tilde{r}(t)=\{\Delta_0(t)+K_P\Delta y_0(t)+K_I(t)y_0(t)+K_D(t)\Delta^2 y_0(t)\}/K_I \quad (9)$$

According to the FRIT method, the output of a reference model with respect to the target value $\tilde{r}(t)$ is designated by $\tilde{y}_m(t)$, and control parameters are determined to reduce the error between $\tilde{y}_m(t)$ and $y_0(t)$.

3. Offline Learning of Data-Oriented PID Control by FRIT Method

Next, the offline learning of the data-oriented PID control by the FRIT method will be described more specifically. First, to calculate the PID gains at the point of request $\varphi_0(t)$ in closed loop data, the distance from the point of request to the information vector in the database is calculated by Equation (5) to select k neighborhood data. Subsequently, the following PID gain $K^{old}(t)$ is calculated by Equation (6) and learned by the steepest descent method to newly derive $K^{new}(t)$. In this manner, the PID gain is updated into the latest data.

$$K^{new}(t) = K^{old}(t) - \eta \frac{\partial J(t+1)}{\partial K(t)} \quad (10)$$

$$\eta = [\eta_P, \eta_I, \eta_D]$$

where $\eta$ indicates the learning rate and $J(t+1)$ indicates the evaluation norm defined by the following Equation (11):

$$J(t+1):=\tfrac{1}{2}E(t+1)^2$$

$$E(t):=y_0(t)-\tilde{y}_m(t) \quad (11)$$

where $\tilde{y}_m(t)$ is designed by the following Equation (12):

$$\tilde{y}_m(t) = \frac{z^{-1}P(1)}{P(z^{-1})}\tilde{r}(t) \quad (12)$$

$P(z^{-1})$ is a characteristic polynomial of the reference model and represented by the following Equations (13):

$$P(z^{-1}) := 1 + p_1 z^{-1} + p_2 z^{-2} \quad (13)$$

$$p_1 = -2\exp\left(-\frac{\rho}{\mu}\right)\cos\left(\frac{\sqrt{4\mu-1}}{2\mu}\right)$$

$$p_2 = \exp\left(-\frac{\rho}{\mu}\right)$$

$$\rho := \frac{T_s}{\sigma}$$

$$\mu := 0.25(1-\delta) + 0.51\delta$$

where $\delta$ indicates a parameter related to the rise characteristic of a control system, $\sigma$ indicates a parameter related to the attenuation characteristic thereof, and $\delta$, $\sigma$ are set arbitrarily during the design process. The partial differentials of the second term on the right side of Equation (10) are expanded in the following manner:

$$\frac{\partial J(t+1)}{\partial K_P(t)} = \frac{\partial J(t+1)}{\partial \tilde{y}_m(t+1)} \frac{\partial \tilde{y}_m(t+1)}{\partial \tilde{r}(t)} \frac{\partial \tilde{r}(t)}{\partial K_P(t)}$$

$$= \frac{E(t+1)P(1)\Delta y_0(t)}{K_I^{old}(t)}$$

$$\frac{\partial J(t+1)}{\partial K_I(t)} = \frac{\partial J(t+1)}{\partial \tilde{y}_m(t+1)} \frac{\partial \tilde{y}_m(t+1)}{\partial \tilde{r}(t)} \frac{\partial \tilde{r}(t)}{\partial K_I(t)} \quad (14)$$

$$= \frac{E(t+1)P(1)\Gamma(t)}{K_I^{old}(t)^2}$$

$$\frac{\partial J(t+1)}{\partial K_D(t)} = \frac{\partial J(t+1)}{\partial \tilde{y}_m(t+1)} \frac{\partial \tilde{y}_m(t+1)}{\partial \tilde{r}(t)} \frac{\partial \tilde{r}(t)}{\partial K_D(t)}$$

$$= \frac{E(t+1)P(1)\Delta^2 y_0(t)}{K_I^{old}(t)}$$

where $\Gamma(t)$ is given by the following Equation (15):

$$\Gamma(t)=-\Delta w_0(t)-K_P^{old}(t)+K_I^{old}(t)y_0(t)+\{K_P^{old}(t)+2K_D^{old}(t)\}y_0(t-1)+K_D^{old}(t)y_0(t-2) \quad (15)$$

Performing the offline learning in this procedure repeatedly until the evaluation norm represented by Equation (11) becomes sufficiently small allows for obtaining an optimum database. In applying the data-oriented control, forming a local controller following the procedure of [STEP 1]-[STEP 3] on a step-by-step basis will achieve control performance that will work even more effectively with respect to a nonlinear system (i.e., a human being's sensitivity).

(2) Second Embodiment

This embodiment is an implementation of the present disclosure as an ankle foot orthosis.

(Circuit Configuration)

Figure 4A:
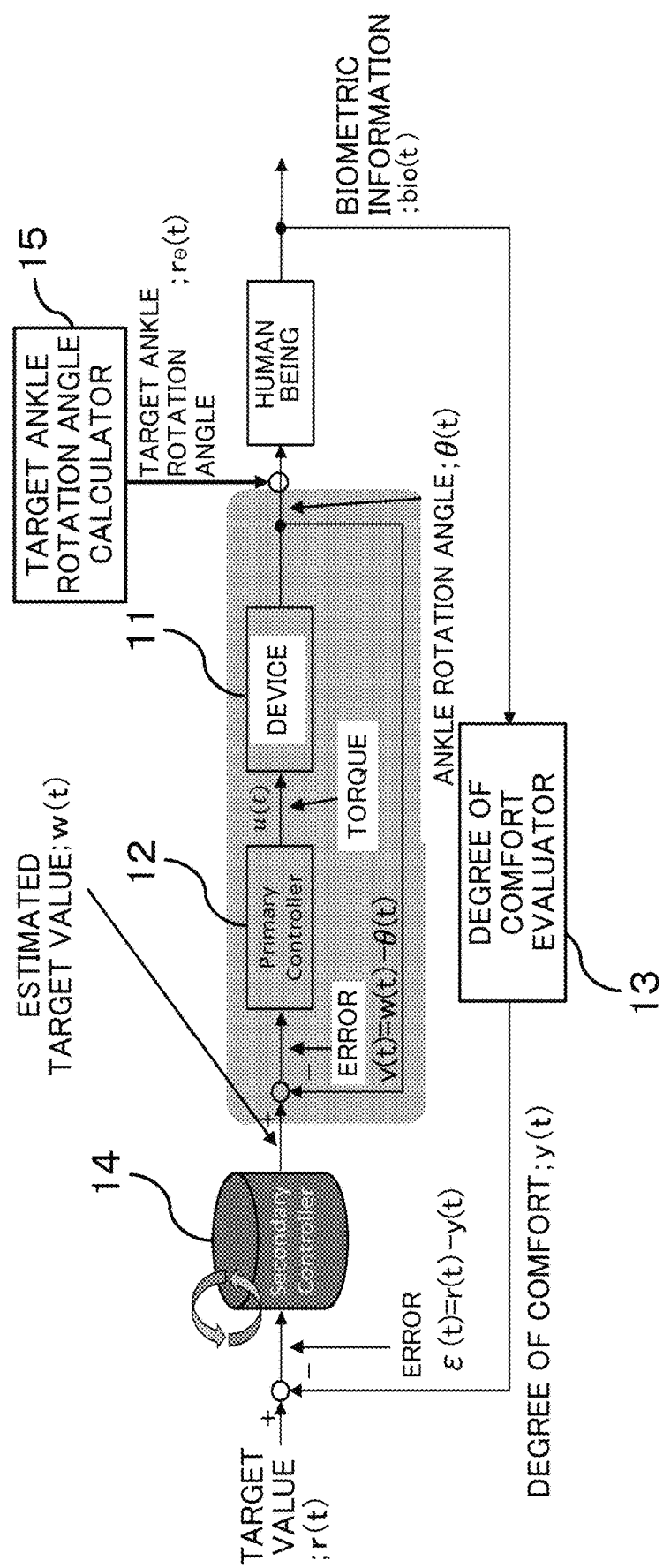
FIG. 4A illustrates an overall configuration for a second embodiment of the present disclosure and FIG. 4B is a photograph showing an exemplary ankle foot orthosis.

FIG. 4A illustrates an overall configuration for this embodiment. In FIG. 4A, an ankle foot orthosis 11 to be a device under control determines the ankle rotation angle $\theta(t)$ with respect to a human being in accordance with an input manipulated variable u(t). A primary controller 12 determines the torque u(t) with respect to the ankle foot orthosis 11 based on an input difference v(t) between an estimated target value w(t) and the ankle rotation angle $\theta(t)$. A degree of comfort evaluator 13 detects biometric information bio(t) about the human being corresponding to the ankle rotation angle $\theta(t)$, evaluates the human being's psychology based on the biometric information bio(t), and determines a degree of comfort y(t) representing the psychology. A secondary controller 14 determines the estimated target value w(t) based on an input difference $\varepsilon(t)$ between a target value r(t) of the human being's psychology and the degree of comfort y(t). A target ankle rotation angle calculator 15 calculates a target ankle rotation angle $r_\theta(t)$. This target ankle rotation angle $r_\theta(t)$ is calculated by a mathematical equation of robotic engineering (as will be described in detail later).

Figure 4B:
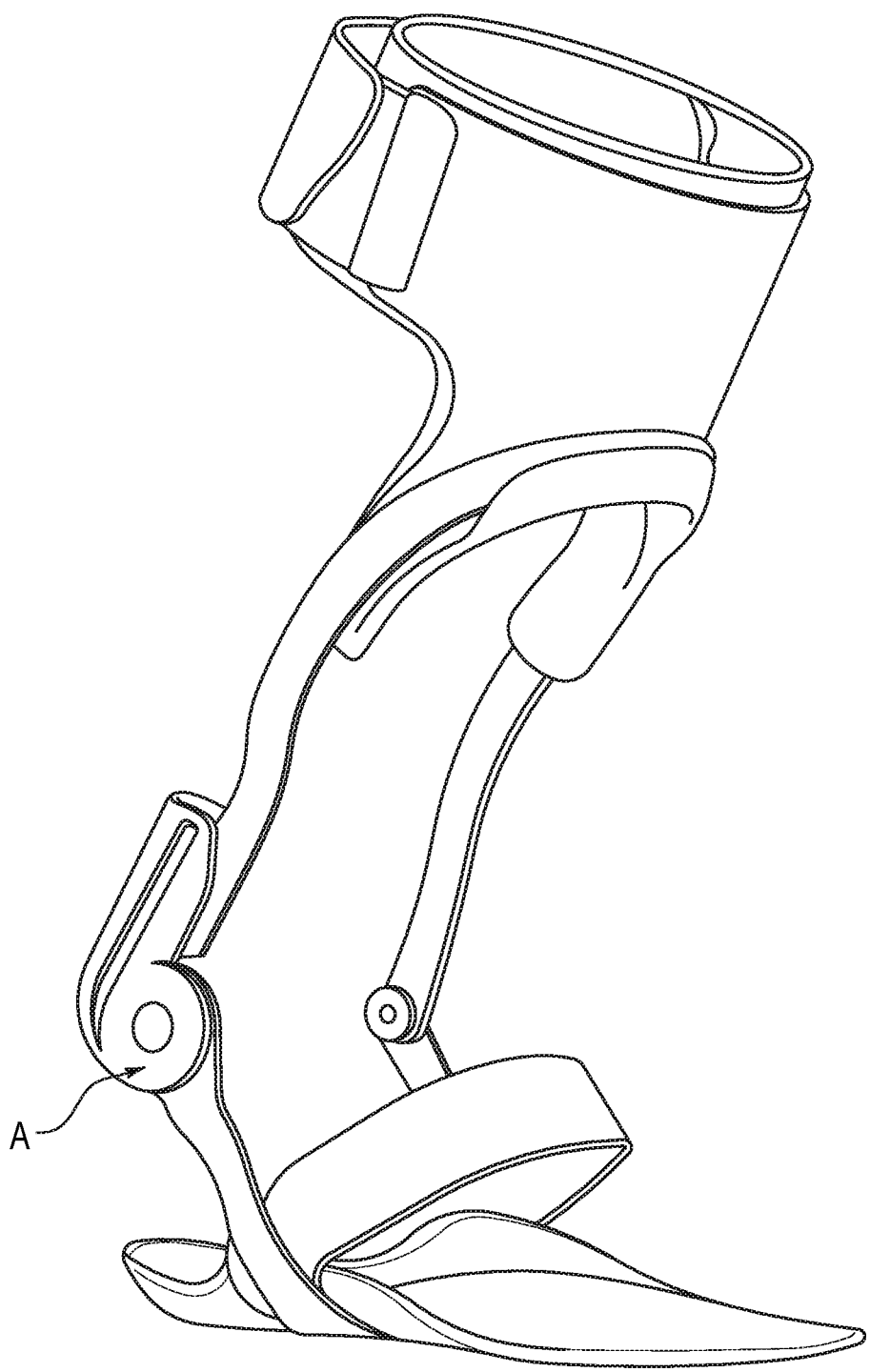

FIG. 4B is an overall view of the ankle foot orthosis, where the rotation of the ankle A is represented by the ankle rotation angle $\theta(t)$.

(Configuration for Degree of Comfort Evaluator)

In this embodiment, the difference e between the ankle rotation angle $\theta(t)$ and the target ankle rotation angle $r_\theta(t)$ is used as the biometric information bio(t) about a human being, and the degree of comfort evaluator 13 outputs a degree of comfort y(t) based on this difference e. This is based on the assumption that if there is any error (difference) between the actual and target ankle rotation angles, the human being's degree of comfort is determined based on the error. More particularly, the following relation is derived by the Weber-Fechner law stating that the intensity of a sensation is proportional to the logarithm of the intensity of the stimulus causing it, where E indicates a constant and varies depending on the human being as a subject.

$$y = \frac{1}{1 + E \cdot \log(1 + e)} \quad (16)$$

Figure 5:
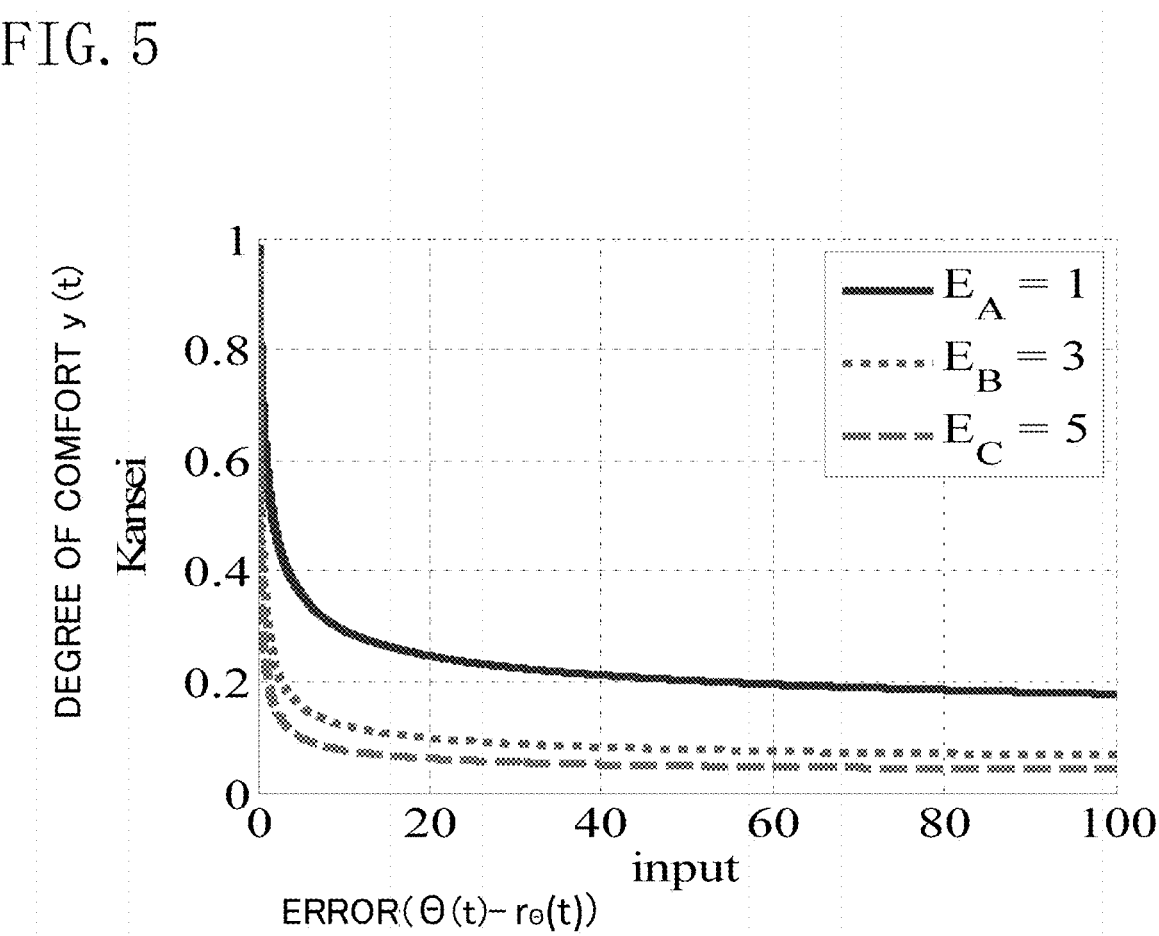
FIG. 5 is a graph showing a relationship between the ankle rotation error and the degree of comfort.

FIG. 5 shows a relationship between the error e and the degree of comfort y(t). As is clear from FIG. 5, the larger the error e, the lower the degree of comfort y(t).

(Configuration for Target Ankle Rotation Angle Calculator)

In this embodiment, the following technique for use in robotic engineering is adopted in which with respect to the target ankle rotation angle $r_\theta(t)$, the ankle rotation angle $\theta(t)$ and the target ankle rotation angle $r_\theta(t)$, which are outputs of the ankle foot orthosis 11, are used as an error that would make the human wearer feel uncomfortable.

According to this embodiment, a location/velocity/acceleration planning method with an n-order polynomial is adopted to generate the target ankle rotation angle $r_\theta(t)$. As used herein, the "polynomial" refers herein to a time function represented by the following Equation (17):

$$r_\theta(t) = a_n t^n + a_{n-1} t^{n-1} + \ldots + a_1 t + a_0 \quad (17)$$

In this Equation (17), n is the degree of the polynomial and is supposed to be a natural number. The coefficient $a_j$ (where j=0, 1, 2, ..., n) is determined based on the initial condition and the terminal condition. Supposing this Equation (17) is a function of location, the velocity and acceleration are respectively a first-order differentiation and a second-order differentiation thereof. Thus, the following two Equations (18) are derived.

$$\dot{r}_\theta(t) = n a_n t^{n-1} + (n-1) a_{n-1} t^{n-2} + \ldots + a_1$$

$$\ddot{r}_\theta(t) = n(n-1) a_n t^{n-2} + (n-1)(n-2) a_{n-1} t^{n-3} + \ldots + 2 a_2 \quad (18)$$

Now, a design procedure in a situation where n=5 will be described. In such a situation, r(t), $\dot{r}(t)$, and $\ddot{r}(t)$ are respectively given by the following Equations (19):

$$r_\theta(t) = a_5 t^5 + a_4 t^4 + a_3 t^3 + a_2 t^2 + a_1 t + a_0$$

$$\dot{r}_\theta(t) = 5 a_5 t^4 + 4 a_4 t^3 + 3 a_3 t^2 + 2 a_2 t + a_1$$

$$\ddot{r}_\theta(t) = 20 a_5 t^3 + 12 a_4 t^2 + 6 a_3 t + 2 a_2 \quad (19)$$

In this case, there are six unknown variables $a_j$. Thus, setting an initial condition t=0 with an initial location $r_\theta(0)$, an initial velocity $\dot{r}_\theta(0)$ and an initial acceleration $\ddot{r}_\theta(0)$ and a terminal condition $t=t_{end}$ with a terminal location $r_\theta(t_{end})$, a terminal velocity $\dot{r}_\theta(t_{end})$ and a terminal acceleration $\ddot{r}_\theta(t_{end})$ allows the unknown variables $a_j$ to be calculated by the following Equations (20):

$$\begin{bmatrix} r_\theta(0) \\ \dot{r}_\theta(0) \\ \ddot{r}_\theta(0) \\ r_\theta(t_{end}) \\ \dot{r}_\theta(t_{end}) \\ \ddot{r}_\theta(t_{end}) \end{bmatrix} = \begin{bmatrix} t_0^5 & t_0^4 & t_0^3 & t_0^2 & t_0 & 1 \\ 5t_0^4 & 4t_0^3 & 3t_0^2 & 2t_0^1 & 1 & 0 \\ 20t_0^3 & 12t_0^2 & 6t_0 & 2 & 0 & 0 \\ t_1^5 & t_1^4 & t_1^3 & t_1^2 & t_1 & 1 \\ 5t_1^4 & 4t_1^3 & 3t_1^2 & 2t_1^1 & 1 & 0 \\ 20t_1^3 & 12t_1^2 & 6t_1 & 2 & 0 & 0 \end{bmatrix} \begin{bmatrix} a_5 \\ a_4 \\ a_3 \\ a_2 \\ a_1 \\ a_0 \end{bmatrix} \quad (20)$$

$$\begin{bmatrix} a_5 \\ a_4 \\ a_3 \\ a_2 \\ a_1 \\ a_0 \end{bmatrix} = \begin{bmatrix} t_0^5 & t_0^4 & t_0^3 & t_0^2 & t_0 & 1 \\ 5t_0^4 & 4t_0^3 & 3t_0^2 & 2t_0^1 & 1 & 0 \\ 20t_0^3 & 12t_0^2 & 6t_0 & 2 & 0 & 0 \\ t_1^5 & t_1^4 & t_1^3 & t_1^2 & t_1 & 1 \\ 5t_1^4 & 4t_1^3 & 3t_1^2 & 2t_1^1 & 1 & 0 \\ 20t_1^3 & 12t_1^2 & 6t_1 & 2 & 0 & 0 \end{bmatrix}^{-1} \begin{bmatrix} r_\theta(0) \\ \dot{r}_\theta(0) \\ \ddot{r}_\theta(0) \\ r_\theta(t_{end}) \\ \dot{r}_\theta(t_{end}) \\ \ddot{r}_\theta(t_{end}) \end{bmatrix}$$

Substituting $a_j$ calculated by these Equations (20) into Equation (17) allows for calculating the target ankle rotation angle $r_\theta(t)$.

(Data Control)

The description of the data control will be omitted herein because the data control of this embodiment is carried out in quite the same way as in the first embodiment.

(Results of Simulations)

Next, the results of simulations according to this embodiment will be described.

Figure 6:
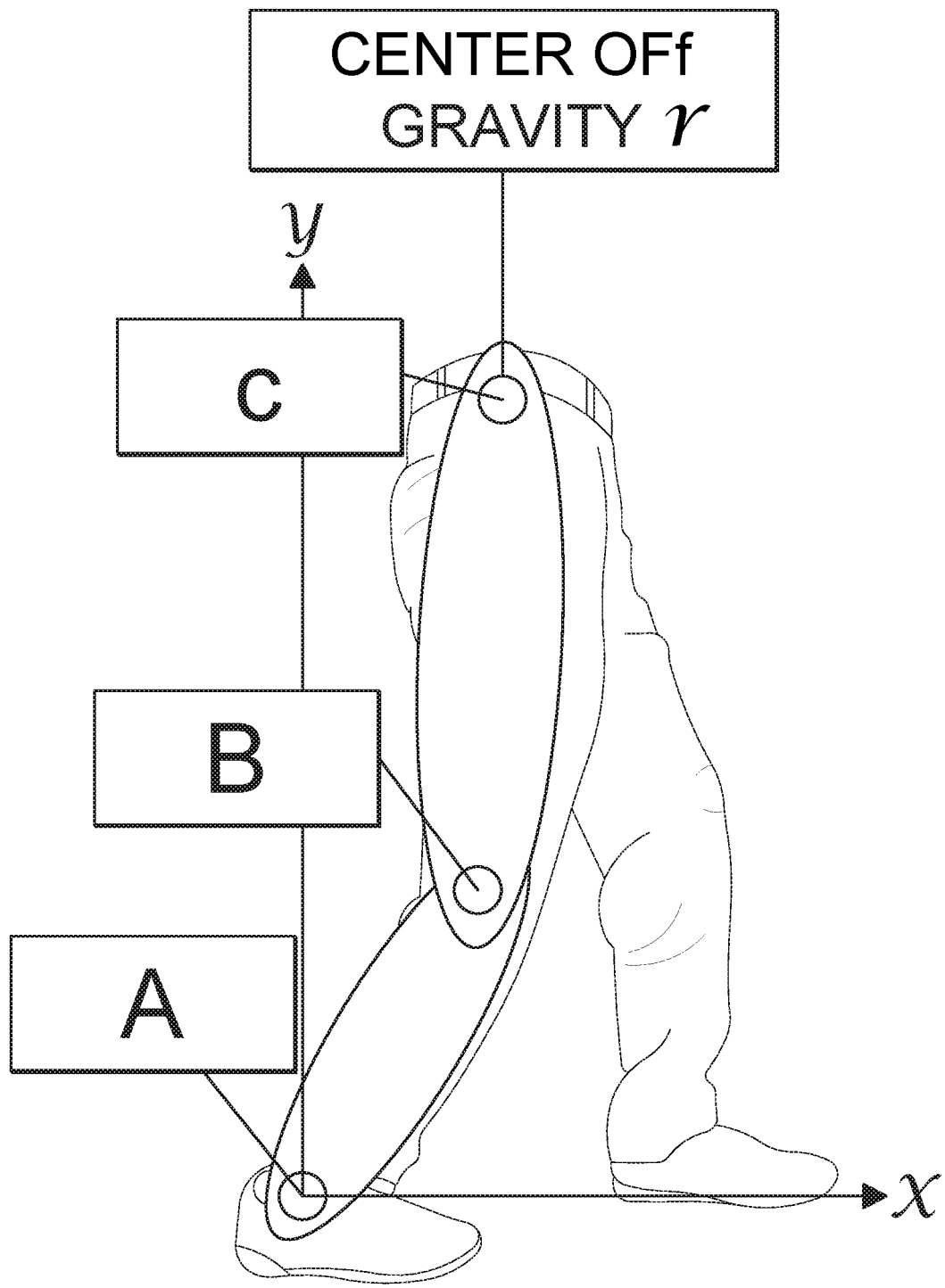
FIG. 6 schematically illustrates the arrangement of a human being's ankle A, knee B and hip C.

FIG. 6 schematically illustrates the arrangement of a human being's ankle A, knee B and hip C to facilitate the understanding of the simulation results.

Figure 7:
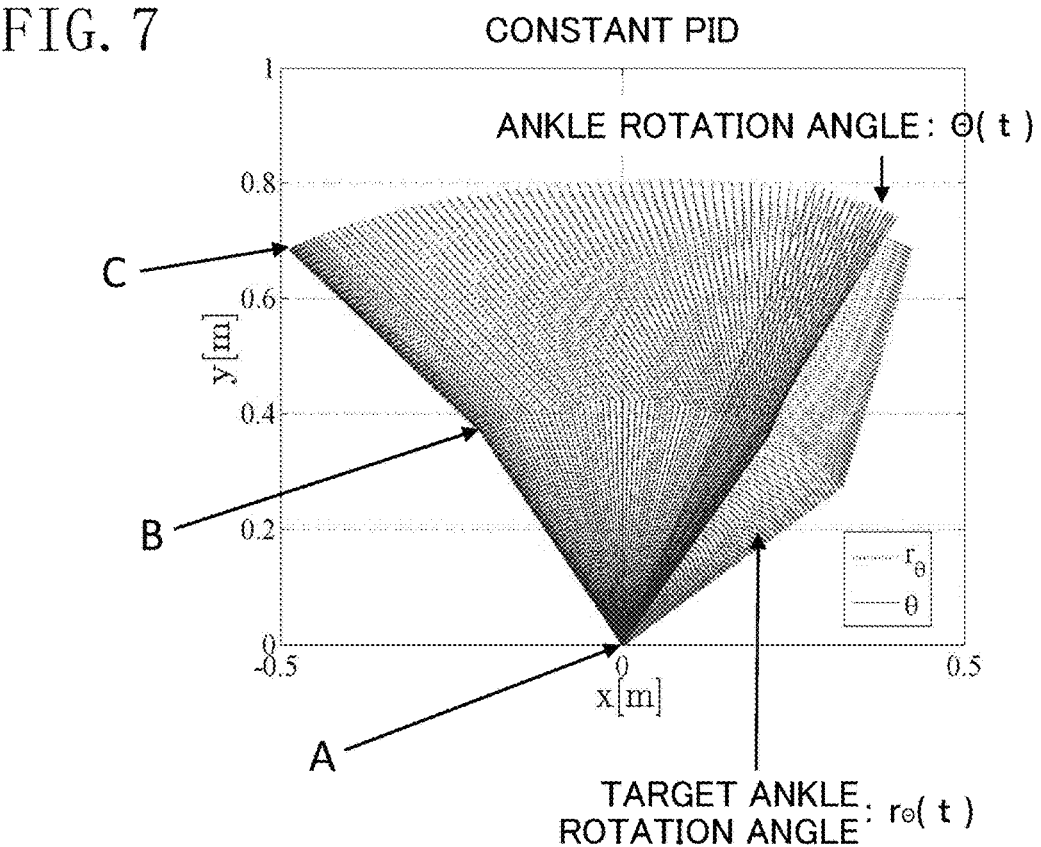
FIG. 7 is a graph showing a relationship between the target ankle rotation angle $r_\theta(t)$ and the ankle rotation angle $\theta(t)$ at a constant PID gain.
Figure 8:
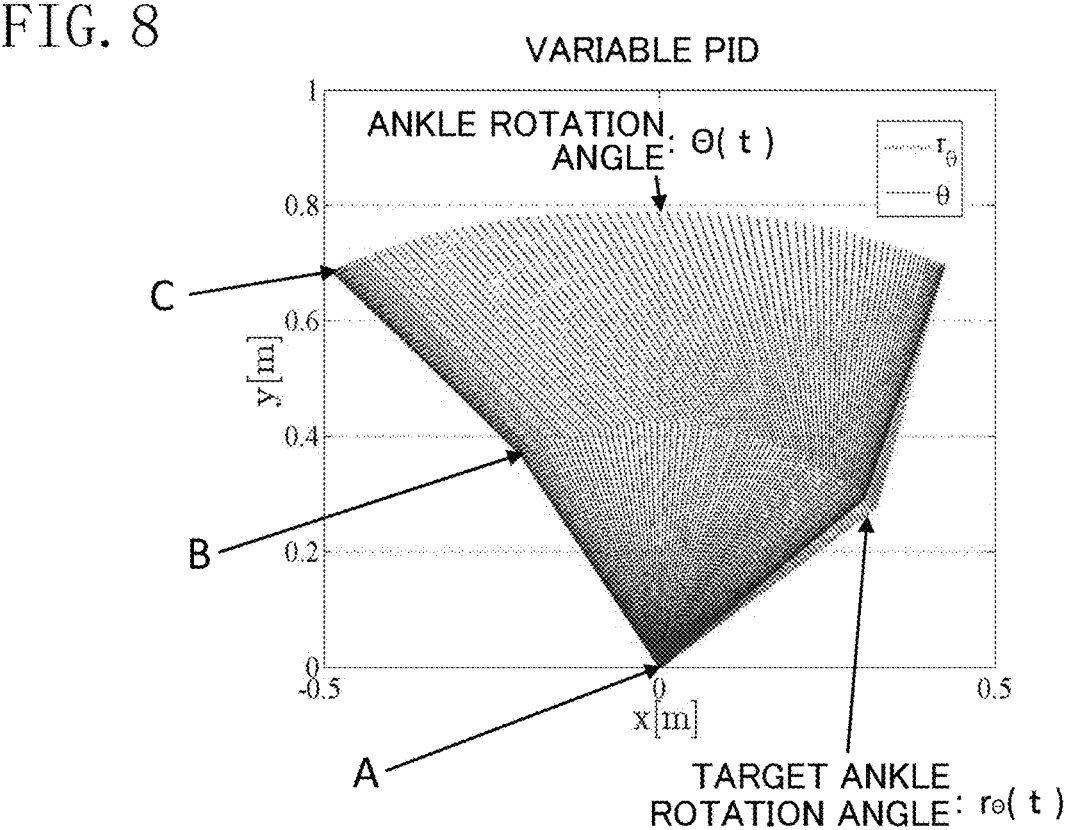
FIG. 8 is a graph showing a relationship between the target ankle rotation angle $r_\theta(t)$ and the ankle rotation angle $\theta(t)$ at variable PID gains.

FIGS. 7 and 8 show the results of the simulations. In FIGS. 7 and 8, A, B and C correspond to the ones shown in FIG. 6. FIG. 7 shows the results obtained when the secondary controller 4 adopted fixed PID gains instead of the data-oriented control. FIG. 8 shows the results of control in which the variable PID gains included in the database were learned based on the input/output data shown in FIG. 7 by applying the technique of the present disclosure.

As can be seen from FIG. 7, a human being can be represented by a nonlinear system, and therefore, the ankle rotation angle (for actual walking) θ(t) cannot follow the target ankle rotation angle (for ideal walking) $r_\theta(t)$ if the PID gains are fixed. On the other hand, as can be seen from the results shown in FIG. 8, learning the PID gains allows the actual walking track to appropriately follow the target walking track. Thus, it can be seen that the present disclosure provides an assistance that helps the wearer follow the target walking track easily.

Embodiments have just been described as examples of the technique disclosed in the present application. The accompanying drawings and detailed description are provided for that purpose.

The components illustrated on the accompanying drawings and described in the detailed description include not only essential components that need to be used to overcome the problem, but also other unessential components that do not have to be used to overcome the problem but are just illustrated or described there to give an example of the technique. Therefore, such unessential components should not be taken for essential ones, simply because such unessential components are illustrated on the drawings or mentioned in the detailed description.

Note that each and every embodiment described above is just an example of the technique of the present disclosure in any respect and should not be construed to be a limiting one. Besides, any variations or modifications, replacements, additions, or omissions falling within the range of equivalents to the claims to be described below are all encompassed within the scope of the present disclosure.

A data-oriented feedback controller and data-oriented feedback control method according to the present disclosure is naturally applicable to not only devices that are designed to directly assist the human being's motion such as an ankle foot orthosis or a walking assist device, but also devices that are designed to indirectly act on the human user such as a consumer electronic appliance like an air conditioner or a means of transportation such as a motor vehicle as well.

What is claimed is:

1. A data-oriented feedback controller comprising:
a first feedback loop; and
a second feedback loop that is nested within the first feedback loop, wherein:
the second feedback loop includes:
a device under control configured to determine a controlled variable θ(t) with respect to a human being in accordance with an input manipulated variable u(t); and
a primary controller configured to determine the manipulated variable u(t) based on an input difference v(t) between an estimated target value w(t) and the controlled variable θ(t);
the first feedback loop includes a psychological evaluator configured to detect biometric information bio(t) about the human being corresponding to the controlled variable θ(t), evaluate the human being's psychology based on the biometric information bio(t), and determine a psychological output value y(t) representing the psychology, wherein the psychological evaluator detects three pieces of information of pleasant/unpleasant, active/inactive, and a sense of expectation as the biometric information bio(t), determines a sensitivity value based on a correlation between these three pieces of information, and regards the sensitivity value as the psychological output value y(t); and
the data-oriented feedback controller further comprises a secondary controller configured to receive a difference ε(t) between a target value r(t) of the human being's psychology and the psychological output value y(t) and determine the estimated target value w(t) based on the difference ε(t).

2. A data-oriented feedback controller comprising:
a first feedback loop; and
a second feedback loop that is nested within the first feedback loop, wherein:
the second feedback loop includes:
a device under control configured to determine a controlled variable θ(t) with respect to a human being in accordance with an input manipulated variable u(t); and
a primary controller configured to determine the manipulated variable u(t) based on an input difference v(t) between an estimated target value w(t) and the controlled variable θ(t);
the first feedback loop includes a psychological evaluator configured to detect biometric information bio(t) about the human being corresponding to the controlled variable θ(t), evaluate the human being's psychology based on the biometric information bio(t), and determine a psychological output value y(t) representing the psychology;
the data-oriented feedback controller further comprises a secondary controller configured to receive a difference ε(t) between a target value r(t) of the human being's psychology and the psychological output value y(t) and determine the estimated target value w(t) based on the difference ε(t); and
the secondary controller sequentially accumulates the target values r(t) of the human being's psychology, the psychological output values y(t), and the estimated target values w(t) in a database, calculates PID gains $K_P$, $K_I$, and $K_D$ based on the data accumulated, and outputs a latest estimated target value w(t) represented by the following equation:

$$w(t) = -K_P y(t) + K_I \int_0^\tau \varepsilon(\tau) d\tau - K_D \frac{dy(t)}{dt}.$$

3. A data-oriented feedback controller comprising:
a first feedback loop; and
a second feedback loop that is nested within the first feedback loop, wherein:
the second feedback loop includes:
a device under control configured to determine a controlled variable θ(t) with respect to a human being in accordance with an input manipulated variable u(t); and
a primary controller configured to determine the manipulated variable u(t) based on an input difference v(t) between an estimated target value w(t) and the controlled variable θ(t);
the first feedback loop includes a psychological evaluator configured to detect biometric information bio(t) about the human being corresponding to the controlled variable θ(t), evaluate the human being's psychology based on the biometric information bio(t), and determine a psychological output value y(t) representing the psychology;
the data-oriented feedback controller further comprises a secondary controller configured to receive a difference ε(t) between a target value r(t) of the human being's psychology and the psychological output value y(t) and determine the estimated target value w(t) based on the difference ε(t); and
the primary controller performs a control operation represented by the following equation in a case that the difference v(t) between the estimated target value w(t) and the controlled variable θ(t) is input to the primary controller and the manipulated variable u(t) is output from the primary controller:

$$u(t) = K_{P1} v(t) + K_{D1} \frac{dv(t)}{dt}$$

(where $K_{P1}$ and $K_{D1}$ are gains of a PD control).

* * * * *